United States Patent [19]
Nickerson et al.

[11] Patent Number: 5,292,252
[45] Date of Patent: Mar. 8, 1994

[54] STIMULATOR HEALING CAP

[75] Inventors: Bruce L. Nickerson, Davie; Chad J. Patterson, Plantation; Richard A. Smolowitz, Davie, all of Fla.

[73] Assignee: Impla-Med, Inc., Sunrise, Fla.

[21] Appl. No.: 990,064

[22] Filed: Dec. 14, 1992

[51] Int. Cl.$^5$ ............................................. A61C 8/00
[52] U.S. Cl. ...................................................... 433/173
[58] Field of Search ................ 433/173, 174, 175, 176

[56] References Cited

U.S. PATENT DOCUMENTS

| | | | |
|---|---|---|---|
| 4,027,392 | 6/1977 | Sawyer et al. | 433/174 |
| 4,175,565 | 11/1979 | Chiarenza et al. | 433/174 X |
| 4,195,367 | 4/1980 | Kraus | 433/173 X |
| 4,856,994 | 8/1989 | Lazzara et al. | 433/173 |
| 5,037,442 | 8/1991 | Wintermantel et al. | 433/173 X |
| 5,145,371 | 9/1992 | Jorneus | 433/174 X |

*Primary Examiner*—Gene Mancene
*Assistant Examiner*—Nicholas D. Lucchesi
*Attorney, Agent, or Firm*—David P. Gordon

[57] ABSTRACT

A stimulator healing cap is disclosed for enhancing and speeding the growth of bone cells and bone tissue surrounding a dental implant. The stimulator healing cap includes a threaded portion which is engagable with an interior threaded portion of the implant and a top portion containing a current source. In one embodiment, the top portion and the threaded portion are conductive and are connected by a middle insulated portion; the threaded portion being coupled to one pole of the current source and the top portion being coupled to the other pole of the current source. In another embodiment, the current source is coupled to a coil wound around a longitudinal core inside the threaded portion. The healing cap provides a current path or electromagnetic field in the vicinity of bone tissue surrounding the implant which stimulates the growth of the bone tissue and speeds up the primary healing phase after the implant is surgically inserted.

14 Claims, 1 Drawing Sheet

STIMULATOR HEALING CAP

BACKGROUND OF THE INVENTION

1. Field of the Invention

This invention relates to dental implants. More particularly, this invention relates to a healing cap temporarily attached to a surgically inserted dental implant which accelerate and enhances the initial or primary healing of the bone which surrounds the implant surgical site.

2. State of the Art

Contemporary dental implant surgery includes the use of certain restorative devices which are inserted on to implants. These restorative devices take the place of natural teeth and are attached to implants which are well integrated into the hard bone tissue so that they are as stable as natural tooth roots. The conventional procedure for inserting a dental implant includes drilling a hole in the maxillary or mandibular jawbone and inserting the implant in the prepared hole. Various types of endosseous dental implants are used: e.g. blades, screws, and cylinders. The implant is generally made of titanium or titanium alloy and the top of the implant is provided with mating means (usually a top portion and inner threads) for attaching the restorative device. Before attaching the restorative device, however, there is typically a healing phase of between three to six months during which time bone tissue grows around the implant so that it becomes well integrated with the adjacent bone.

During the initial and primary healing phase, a cover screw is usually attached to the top of the implant to maintain the integrity of the top portion and inner threads of the implant. After the healing phase is completed and bone integration has successfully occurred, the cover screw is removed and discarded and the restorative phase of the treatment can be initiated.

It is a clear disadvantage of the conventional procedure that there be such a long delay between the time of insertion of the implant and the time when a restoration can be made for the patient. Unfortunately, it usually takes this length of time for the bone forming cells and bone tissue surrounding the implant to mature sufficiently to adequately hold the implant so that the final restoration will be firmly and properly anchored.

It is known in the medical arts that bone growth can be stimulated by passing an electrical current or an electromagnetic field through the bone. Such techniques have been used for some time in the mending of broken bones in limbs. It has not been known, however, to use this technique to stimulate bone growth for the purpose of shortening the bone healing phase in dental implant surgery.

SUMMARY OF THE INVENTION

It is therefore an object of the invention to provide an apparatus which applies an electrical current or electromagnetic field to the bone forming cells surrounding a dental implant so that bone growth is more efficiently stimulated.

It is also an object of the invention to provide a device which attaches to a dental implant in the same manner as a conventional cover screw, but which stimulates bone growth around and through the entire dental implant.

It is another object of the invention to provide a dental bone stimulating device which includes a self-contained power source which will supply a constant current or electromagnetic field through the bone tissue surrounding a dental implant.

It is a further object of the invention to provide an apparatus which applies an electrical current or electromagnetic field to bone tissue surrounding a dental implant, and at the sam time provides the same protection for the top portion and inner threads of the implant as would a conventional cover screw.

In accord with these objects which will be discussed in detail below, a stimulator healing cap is provided, and generally includes a top cap portion containing a current source, and a threaded portion which attaches to the implant in the same way as a cover screw. The current source has a positive and a negative pole, with one of the poles being coupled to the threaded portion and the other pole being coupled to the top portion such that current flows through the implant and the surrounding bone tissue In an alternative embodiment, the current source is coupled to a coil which surrounds a longitudinal core creating an electromagnetic field around the implant and thus in the surrounding bone tissue.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
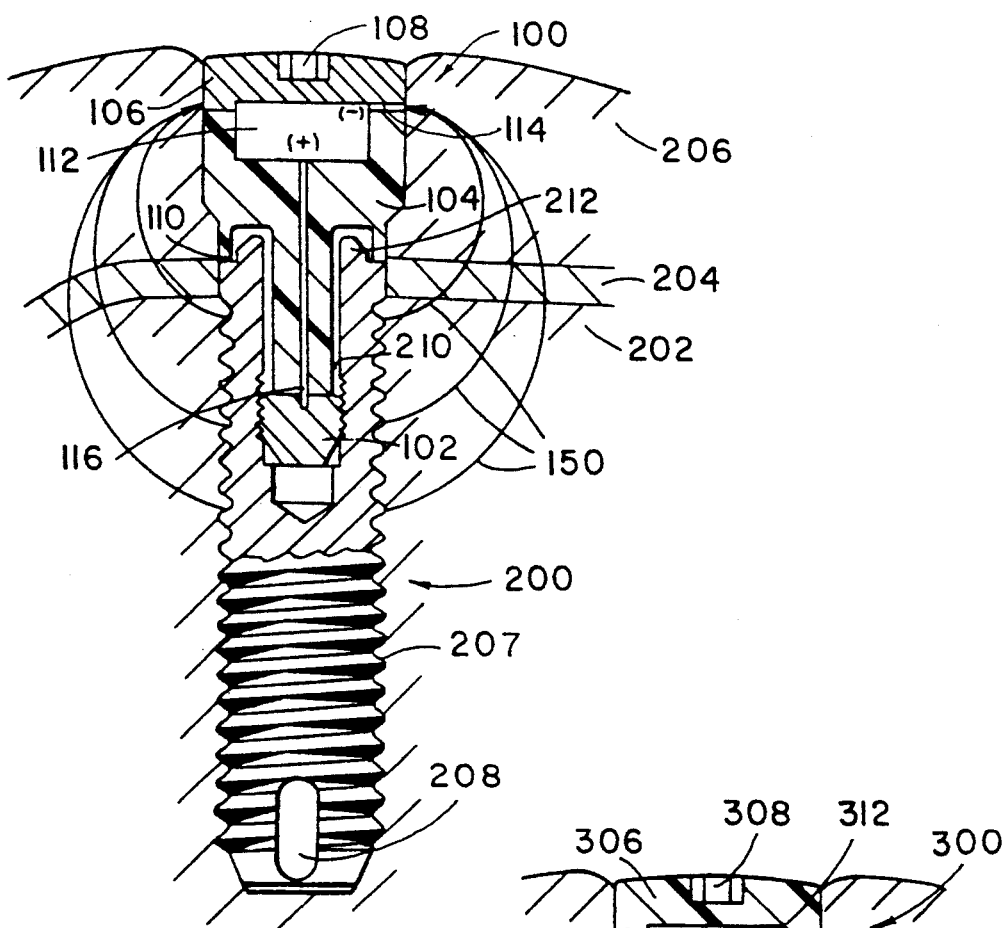
FIG. 1 is a cross sectional view of a first embodiment of the stimulator healing cap of the invention as it is attached to dental implant.

Referring now to FIG. 1, the stimulator healing cap 100 of the invention is shown attached to a dental implant 200. The implant 200 is shown installed in the maxillary or mandibular bon below the cortical plate 204 and the gingiva 206. As can be seen in FIG. 1, the implant 200 is provided with an exterior thread 207 for threading into the bone, and a hole 208 into which bone can grow. Of course, implant 200 could be of the cylindrical type having no threads. Implant 200 is also provided with an interior threaded portion 210 and a top portion 212 for attaching to a prosthetic device (not shown). The top portion 212 of the implant 200, which may take the form of an external hexagonal nut, may extend slightly above the cortical plate 204 and into the gingiva 206. Without any other attachment, the interior threaded portion 210 of the implant 200 is exposed to the gingiva 206. Typically, a temporary cap is provided and screwed into the threaded portion 210 of implant 200 during the initial or primary healing period which occurs after implantation, and before attaching any restorations.

In accord with the invention, a stimulator healing cap 100 is provided. The stimulator healing cap 100 has a conductive threaded portion 102 which enters and engages the threaded portion 210 of the implant 200 as shown in FIG. 1, and a top portion 106 containing a current source 112. The threaded portion 102 of the healing cap 100 is connected to the top portion 106 but is electrically insulated therefrom by an insulated middle portion 104. The insulated middle portion 104 is preferably provided wit a shoulder or flange 110 which covers and protects the top portion 212 of implant 200. The top portion 106 of the healing cap 100 is preferably provided with an upper socket 108 which is engaged by a wrench or driver (not shown) for attaching the healing cap 100 to the implant 200 and for detaching it after the healing phase. The upper socket 108 is not absolutely required, as the healing cap 100 could also be screwed into the implant by gripping the outer surface of the top portion 106 and/or middle portion 104.

As aforementioned, the stimulator healing cap 100 is provided with a current source 112, which may take the form of a small flat battery. The anode of the battery 112 is connected at its pole through the insulated conductor 116 to the threaded portion 102, and the cathode is connected through conductor 114 to the conductive exterior of top portion 106. Of course, if desired, the locations of the anode and cathode may be switched.

It will be appreciated that due to the conductivity of the threaded portion 102, the implant 200 and the top portion 106, and due to the placement of the insulated middle portion 104, a current path indicated by lines 150 is established between the implant 200 through the bone 202, the cortical plate 204 and the gingiva 206 to the top portion 106 of the healing cap 100. This current path stimulates the growth of bone tissue in the maxillary or mandible in the vicinity of the implant 200, thereby shortening the length of the healing phase.

Figure 2:
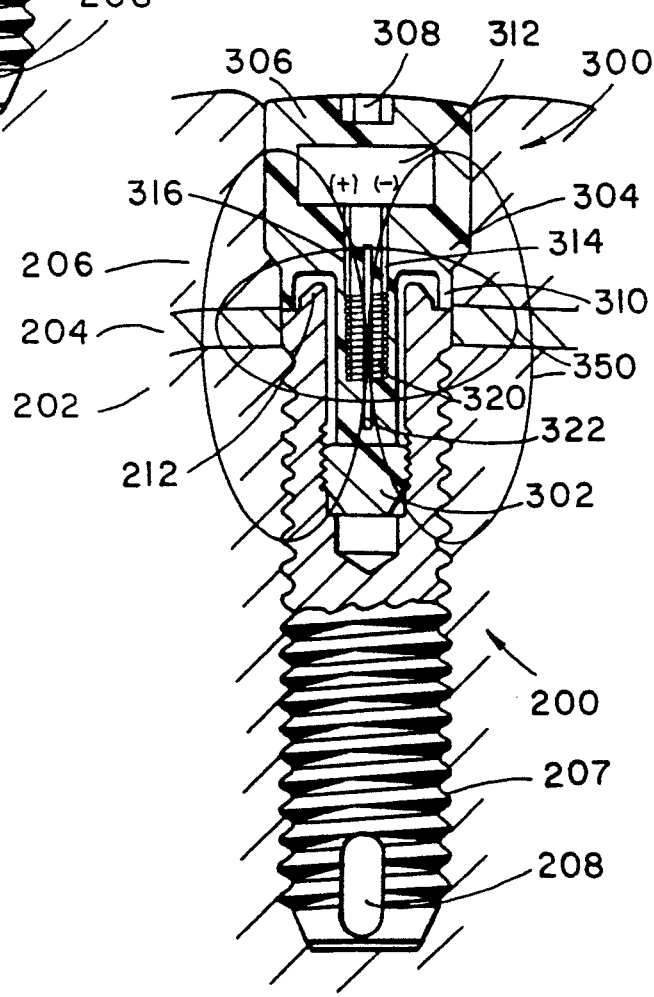
FIG. 2 is a view similar to FIG. 1, but of a second embodiment of the invention.

Turning now to FIG. 2, an alternate embodiment of the healing cap is shown. Here, healing cap 300 also includes a top portion 306 having an upper socket 308 and a middle portion 304 connected to a threaded portion 302. As in the first embodiment, a current source 312 is provided in the top portion 306 and the middle portion is provided with a shoulder or flange 310 which covers and protects the implant 200. In this embodiment, however, none of these portions of the healing cap need to be conductive. In the embodiment of FIG. 2, the healing cap includes a ferrous core 322 extending longitudinally through at least a portion of the cap 300, preferably from the top of the middle portion 304 through to the threaded portion 302. Core 322 is wound with a coil 320 whose ends are coupled to the poles of current source 312 by conductors 314, 316 thereby creating an electromagnet within the healing cap 300.

It will be appreciated that the electromagnet created inside the healing cap 300 by coil 320 receiving current from current source 312 generates a magnetic field 350 as shown in FIG. 2 which promotes bone tissue growth in the vicinity of implant 200 substantially shortening the length of the healing phase.

There have been described and illustrated herein embodiments of a stimulator healing cap. While particular embodiments of the invention have been described, it is not intended that the invention be limited thereto, as it is intended that the invention be as broad in scope as the art will allow and that the specification be read likewise. Thus, while the power source has been disclosed as contained within the top portion of the healing cap, it will be appreciated by those skilled in the art that the power source could be contained in the middle portion or could be spread throughout the healing cap with appropriate insulation. Similarly, while the healing cap has been described as having a threaded portion and the threaded portion is shown in the drawing as relatively small, it will be appreciated that the threaded portion could be larger and in particular in the embodiment of FIG. 2, the threaded portion could include all or part of the middle portion. Also, while the healing cap has been shown to have an hexagonal socket in its top part, any other shape socket or driver receiving means could be used. Moreover, while certain connections between the poles of the power source and the portion of the healing cap have been described and shown, it will be understood by those skilled in the art that other types of connections could be used to achieve substantially the same results in substantially the same way. It will therefore be appreciated by those skilled in the art that yet other modifications could be made to the provided invention without deviating from its spirit and scope as so claimed.

What is claimed is:

1. A stimulator healing cap for enhancing in a patient the growth of bone cells and bone tissue surrounding a dental implant having and a threaded open interior portion having a proximal opening located near the gingival-cortical plate interface in the patient, said stimulator healing cap comprising:
    a) a conductive threaded first portion having a longitudinal axis which threads in and matingly engages in the open threaded interior portion of the implant, wherein an unthreading of said conductive threaded first portion from the threaded open interior portion of the dental implant disengages said stimulator healing cap from the dental implant;
    b) a conductive second portion axially removed from the conductive threaded first portion along said longitudinal axis, and adapted to reside substantially in the gingiva of the patient;
    c) an insulated third portion insulating said conductive second portion from said conductive threaded first portion, and adapted to extend outside the implant; and
    d) a current source having two poles, with a first of said two poles being electrically coupled to said conductive second portion, and the other of said two poles being electrically coupled to said threaded conductive first portion.

2. A stimulator healing cap according to claim 1, wherein:
    said insulated third portion extends into the threaded open interior portion of the dental implant when mounted thereon.

3. A stimulator healing cap according to claim 2, wherein:
    said conductive second portion is a top portion of said stimulator healing cap, and said insulated third portion is a middle portion of said stimulator healing cap.

4. A stimulator healing cap according to claim 3, wherein the dental implant has a top radially protruding mating element, wherein
    said middle portion is provided with a shoulder for covering and protecting said the top radially protruding mating element of said the implant.

5. A stimulator healing cap according to claim 3, wherein
    an outside surface of said conductive top portion is provided with socket means for engaging a driving tool.

6. A stimulator healing cap according to claim 3, wherein:
    said current source is a battery, and said battery is located at least partially in said insulated third portion with one of said poles of said battery coupled to said conductive second portion.

7. A stimulator healing cap according to claim 1, wherein:
said current source is a battery.

8. A stimulator healing cap according to claim 7, wherein:
said battery is located at least partially in said insulated third portion with one of said poles of said battery coupled to said conductive second portion.

9. A stimulator healing cap to speed the growth of bone tissue surrounding a dental implant having an open interior portion, comprising:
a) a first portion which engages the interior portion of the implant, said first portion having a bore therein;
b) a top portion;
c) a current source located in said top portion; and
d) a coil extending in said bore of said first portion, said coil coupled to said current source such that an electromagnetic field is generated by said coil.

10. A stimulator healing cap according to claim 9, where the interior portion of the implant has threads, wherein:
said first portion of said stimulator healing cap has outer threads which engage the threads of the interior portion of the implant.

11. A stimulator healing cap according to claim 10, further comprising:
e) a ferrous core extending longitudinally through said coil.

12. A stimulator healing cap according to claim 9, wherein:
when said first portion is threaded into the threaded interior portion of the dental implant, said first portion of said stimulator healing cap extends into the gingiva of a patient.

13. A stimulator healing cap according to claim 12, wherein the dental implant has a top protruding mating element, wherein
said first portion of said stimulator healing cap is provide with a shoulder for covering and protecting the top protruding mating element of the implant.

14. A stimulator healing cap according to claim 13, wherein
said first portion is provided with socket means for engaging a driving tool.

* * * * *